United States Patent [19]

Oei

[11] Patent Number: 5,774,227
[45] Date of Patent: Jun. 30, 1998

[54] ANOMALLY DETECTION MACHINE FOR FABRICATED PARTS FORMED ON A CARRIER STRIP AND METHOD OF USE

[75] Inventor: Ivan KiatHong Oei, San Diego, Calif.

[73] Assignee: The Whitaker Corporation, Wilmington, Del.

[21] Appl. No.: 790,034

[22] Filed: Jan. 28, 1997

[51] Int. Cl.⁶ .................................................. G01N 21/89
[52] U.S. Cl. ................ 356/430; 250/559.03; 250/559.46
[58] Field of Search ....................... 356/430; 250/559.03, 250/559.26, 559.34, 559.37, 559.45, 559.46

[56] References Cited

U.S. PATENT DOCUMENTS

| | | |
|---|---|---|
| 4,129,384 | 12/1978 | Walker et al. ........................... 356/381 |
| 4,168,126 | 9/1979 | Altman et al. ........................... 356/386 |
| 4,217,053 | 8/1980 | Lavanchy ................................ 356/372 |
| 4,427,296 | 1/1984 | Demarest et al. ...................... 356/387 |
| 4,521,112 | 6/1985 | Kuwabara et al. ..................... 356/375 |
| 4,521,113 | 6/1985 | Kuwabara et al. ..................... 356/387 |
| 4,622,740 | 11/1986 | Mirley, Jr. et al. ....................... 29/715 |
| 5,212,390 | 5/1993 | LeBeau . |
| 5,303,462 | 4/1994 | Chitwood et al. ........................ 29/705 |

Primary Examiner—Vincent P. McGraw
Attorney, Agent, or Firm—Mary K. VanAtten

[57] ABSTRACT

The invention is directed to a machine for detecting anomalies in parts. A strip of parts (10) is transported through a sensor unit having light sources and photodetector pairs (118, 116; 132, 134; 136, 138) to detect pilot holes and the presence and position of parts. At least one of the light sources (136) is directed at an angle to detect out of plane deformations. Simple light sources and photodetectors are used to detect and identity misaligned contacts without the need for complex vision system components.

22 Claims, 8 Drawing Sheets

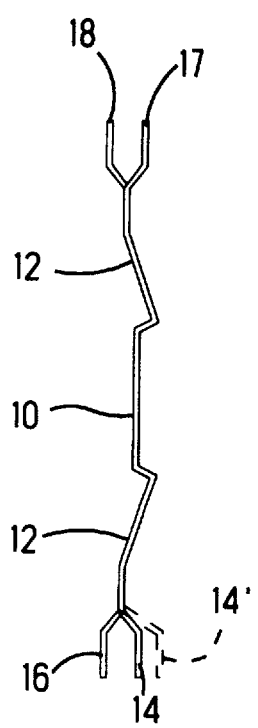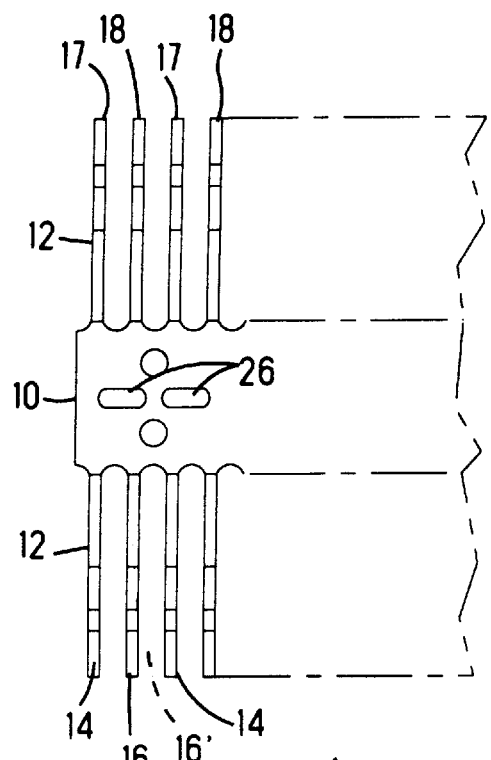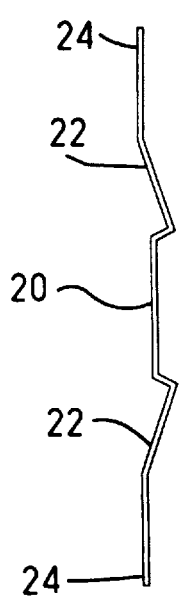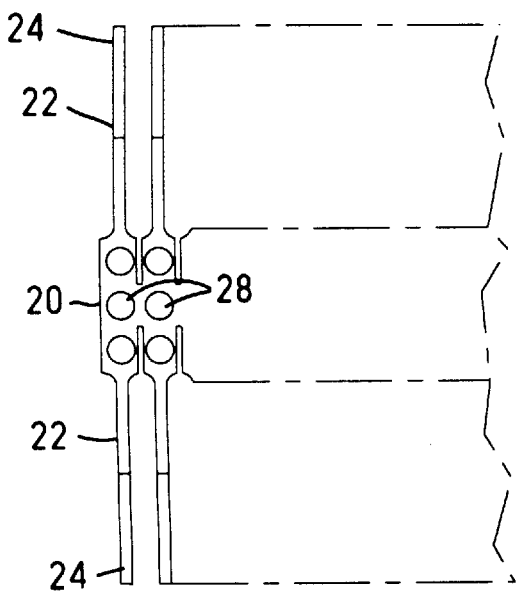

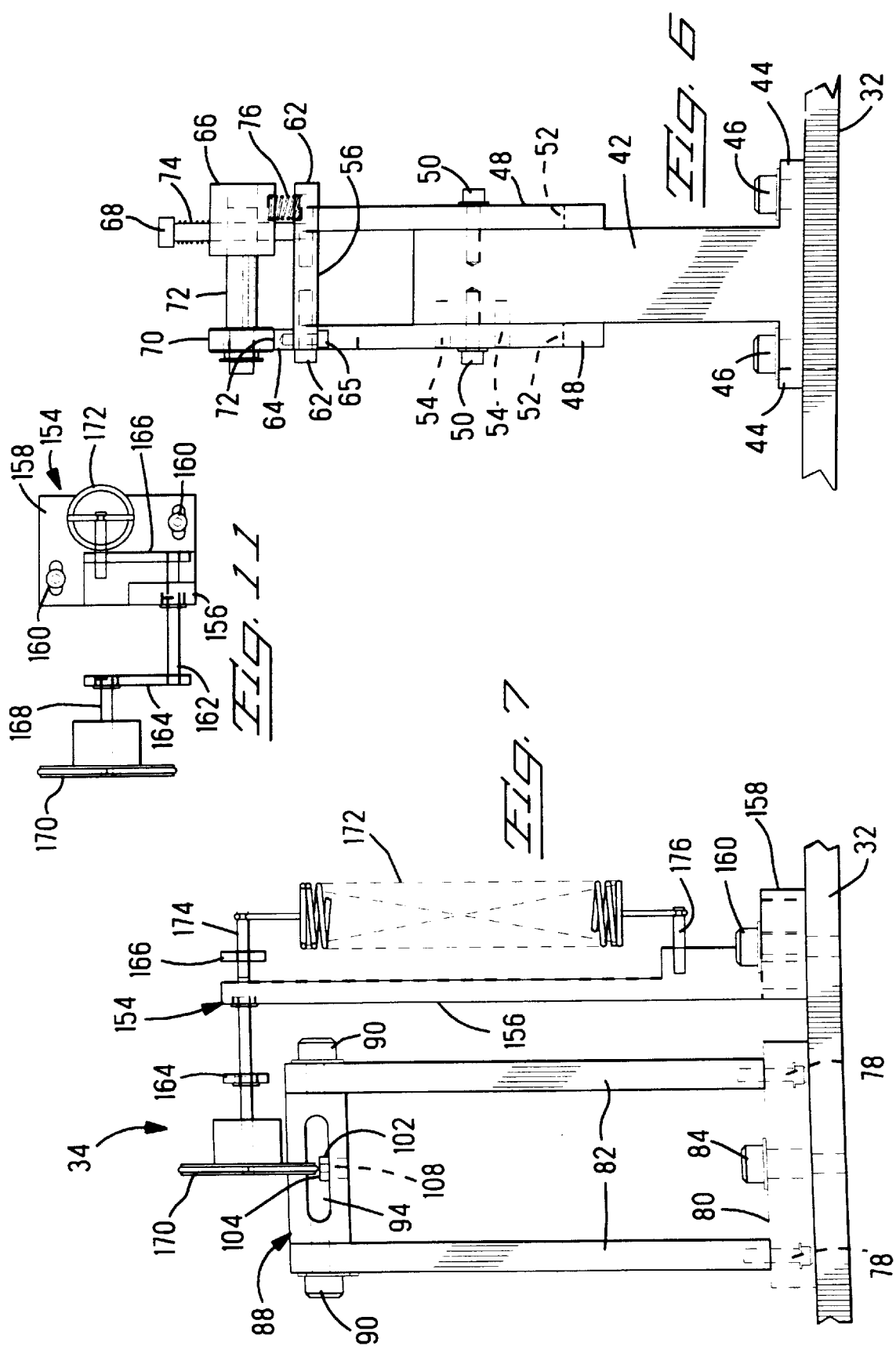

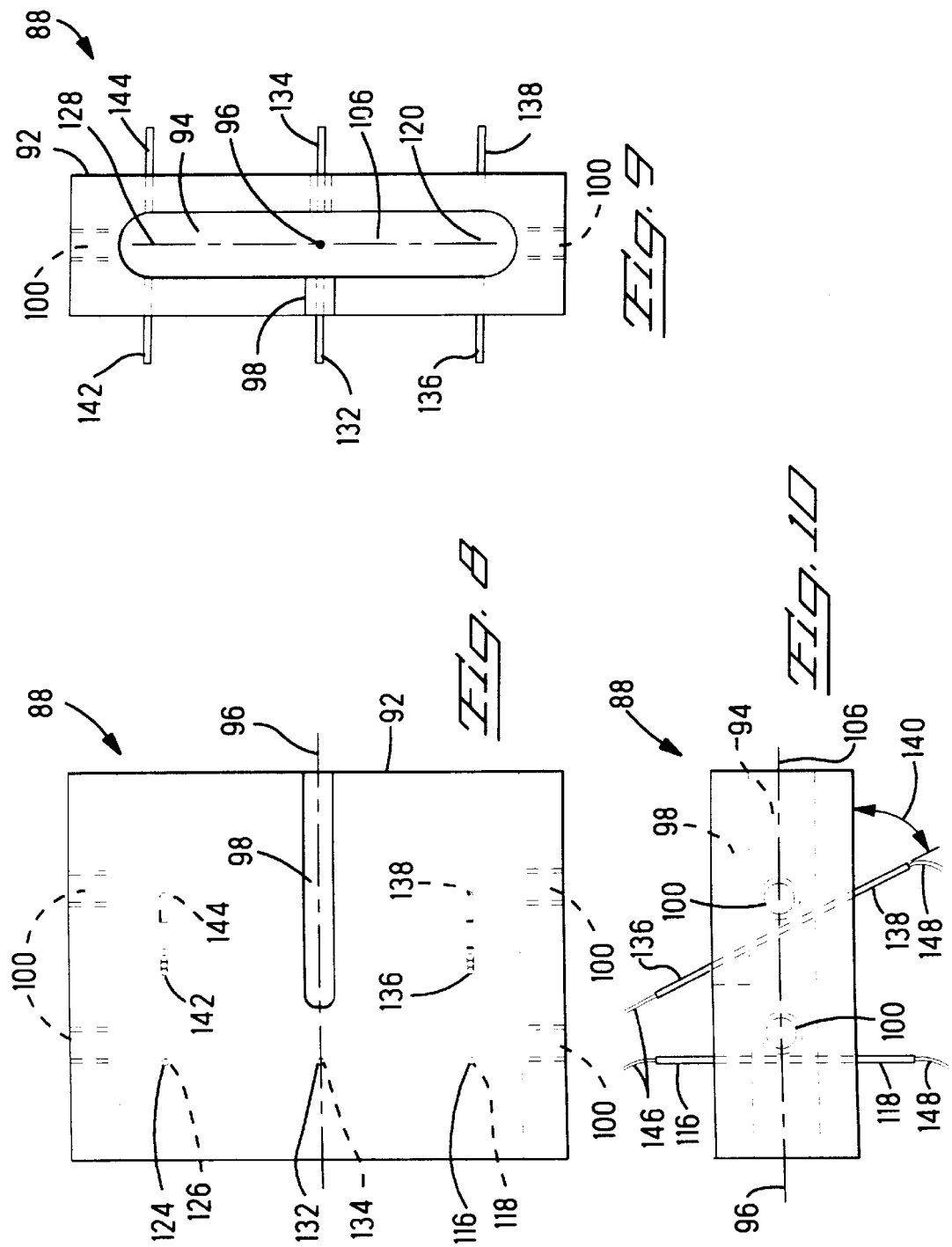

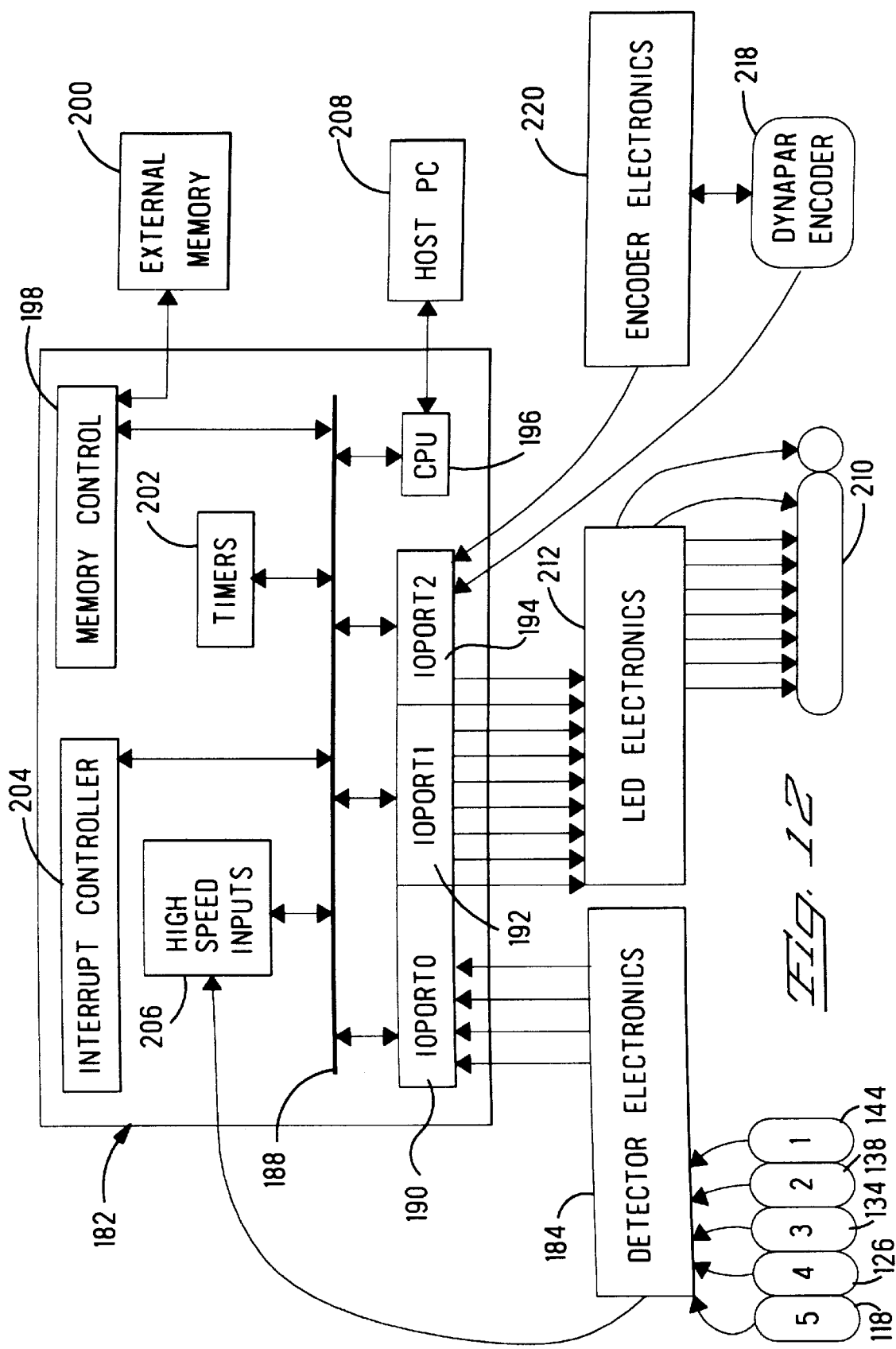

POSITIVE EDGE-TRIGGER-FLIP-FLOP

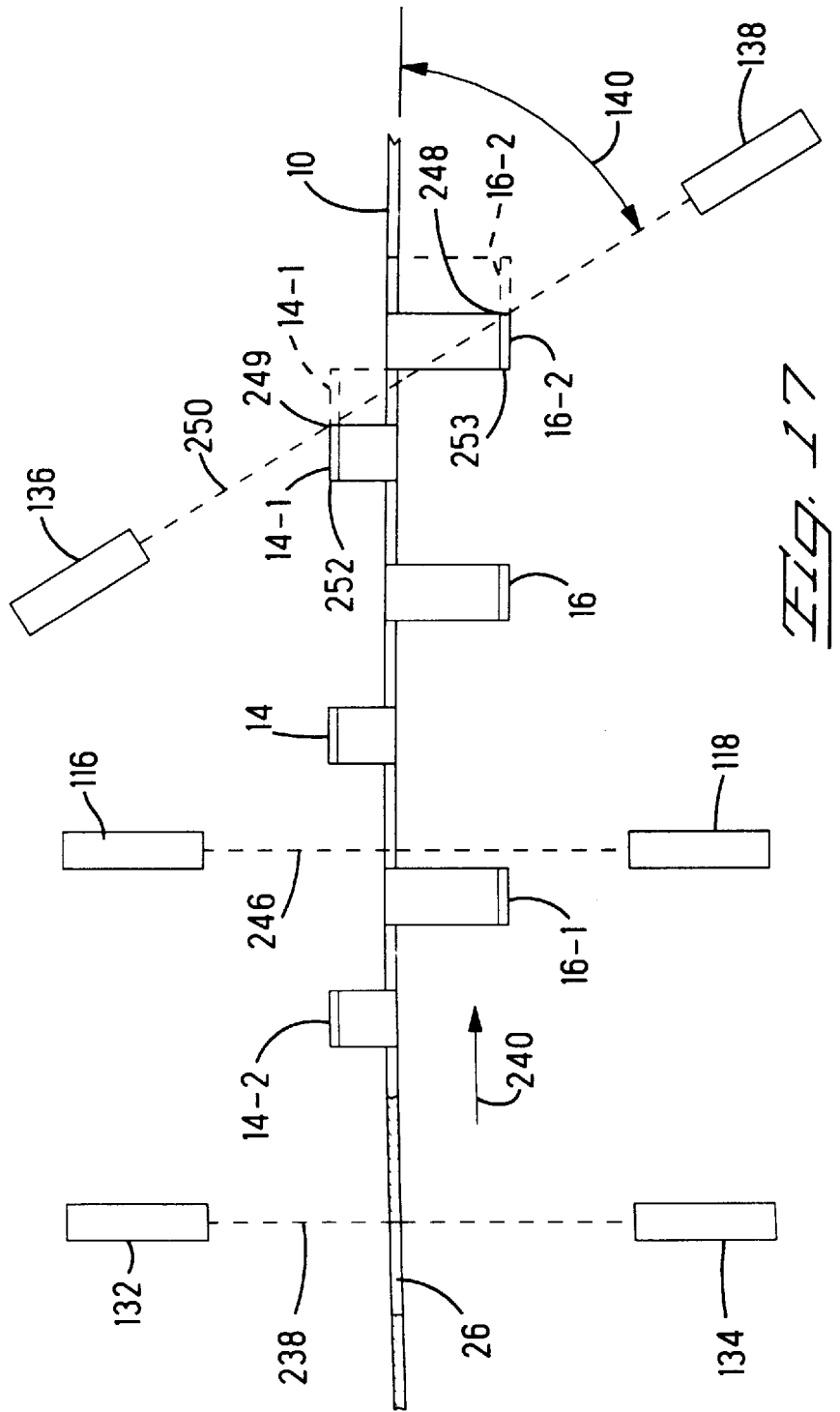

ANOMALLY DETECTION MACHINE FOR FABRICATED PARTS FORMED ON A CARRIER STRIP AND METHOD OF USE

The present invention relates to a machine for detecting certain anomalies of a strip of similar fabricated parts such as electrical contacts that have been stamped and formed on a common carrier strip.

BACKGROUND OF THE INVENTION

In the manufacture of delicate parts attached to a continuous carrier strip, such as stamped and formed electrical contacts for use in electrical connectors, the carrier strip with attached parts is usually wound onto a reel for transport to another manufacturing station where the parts are used in another manufacturing operation In the case where the parts are electrical contacts the carrier strip may be dereeled and fed into a machine where the contacts are severed from the carrier strip and inserted into a connector housing, or some other operation is performed with the contacts. The machinery that handle these delicate parts require that the parts be of a specified size and shape and that all of the parts be uniformly positioned along the carrier strip. Any deviations from this can result in a jammed machine, damaged tooling or product, and possibly a defective or deformed contact that is unknowingly inserted into an otherwise good connector housing that goes undetected Modern stamping and forming machines in wide use today, reliably produce small delicate parts that are of a specified size and shape. However, as the carrier strip is wound onto a reel, there can sometimes be a snag or an undesirable vibration that causes one or more contacts to become misaligned with respect to the carrier strip. Similarly, rough handling of the wound reels during transportation and storage, and even the dereeling operation itself can contribute to misaligned contacts. An example of one kind of parts to which the present invention is directed is shown in FIGS. 1 and 2. A carrier strip 10 is shown having a plurality of contact beams 12 extending from opposite sides of the carrier strip. Each beam 12 terminates in an electrical contact 14 or 16 on the left side of the carrier strip and an electrical contact 17 or 18 on the right side. In the present example the contacts 14 and 17 are bent upwardly and the contacts 16 and 18 are bent downwardly, as best seen in FIG. 2. These contacts, as shown in FIG. 1, are quite small and have a center to center spacing of 0.050 inch. FIGS. 3 and 4 show a carrier strip 20 having a plurality of contact beams 22 and electrical contacts 24, similar to those shown in FIGS. 1 and 2 except that the contacts 24 are not alternately bent upwardly and downwardly, but rather are all in mutual alignment. Both carrier strips 10 and 20 include spaced pilot holes 26 and 28 respectively that were used in the stamping and forming process when the contacts were manufactured and are very accurately positioned with respect to the contacts. There are many variations of carrier strip and contact structures in use, these being only two examples. When a contact becomes misaligned it may be displaced longitudinally with respect to the length of the carrier strip and will be called an X-axis deformation, as shown in phantom lines at 16' in FIG. 1, or it may be displaced laterally and called a Z-axis deformation, as shown in phantom lines at 14'in FIG. 2. It would be advantageous to detect such misalignments prior to feeding the strip of contacts into a machine for processing. Due to the very large numbers of such contacts being used in manufacturing, manual inspection is not practical. Automated inspection systems currently known in the industry typically utilize vision systems, which are very complex and expensive to implement and to maintain. These vision systems usually utilize scanning devices that require rotating mirrors or other moving optical components. The reliability of such systems suffers somewhat, partly due to their complexity and partly due to the difficulty of masking and identifying very small parts.

What is needed is an automated anomaly detection system that will reliably detect small misaligned contacts that is relatively simple and inexpensive to make and is easy to operate and maintain.

SUMMARY OF THE INVENTION

A method and apparatus is disclosed for identifying anomalies in a plurality of spaced parts attached to a common carrier strip. The carrier strip includes a plurality of spaced pilot holes having a known center to center spacing that can be spatially related to the parts. The anomalies to be identified include deformation or misalignment of one or more of the parts with respect to the other parts and the carrier strip. The carrier strip and attached parts is transported along a feed path. A first light source and first photodetector pair are arranged on opposite sides of the feed path so that light from the first light source extends along a first line disposed at a first angle to the feed path, in alignment with a portion of the feed path traversed by the plurality of pilot holes. When a pilot hole is moved into alignment with the first line the first photodetector receives light from the first light source and generates a first positive signal. A second light source and second photodetector pair are arranged on opposite sides of the feed path so that light from the second light source extends along a second line disposed at a second angle to the feed path and through a portion of the feed path traversed by the parts. When the part interrupts the light the second photodetector generates a second negative signal in response thereto and when a part moves out of the path of the light so that the light is no longer interrupted the second photodetector generates a second positive signal A third light source and third photodetector pair are arranged on opposite sides of the feed path so that light from the second light source extends along a third line disposed at a third angle to the feed path that is different from the second angle and through a portion of the feed path traversed by the parts. When a part interrupts the light the third photodetector generates a third negative signal in response thereto and when the part moves out of alignment with the light so that the light is no longer interrupted by the part the third photodetector generates a third positive signal. The anomalies are identified in response to the first and third positive signals and the second and third negative signals The detection of the anomalies results in the generation of an error signal.

DESCRIPTION OF THE FIGURES

FIGS. 1 and 2 are plan and end views, respectively, of a carrier strip and attached electrical contacts;

FIGS. 3 and 4 are views similar to those of FIGS. 1 and 2 showing a different carrier strip and attached electrical terminals;

FIG. 6 is a cross-sectional view taken along the lines 6—6 in FIG. 5;

FIG. 7 is a cross-sectional view taken along the lines 7—7 in FIG. 5;

FIGS. 8, 9, and 10 are plan, side, and front views, respectively, of the sensor unit shown in FIG. 5;

FIG. 11 is a top view of the detector unit shown in FIG. 5;

FIG. 12 is a block diagram showing the control unit and its interconnection to other electrical components of the machine;

FIG. 17 is a schematic representation of the through beam sensors in relation to a carrier strip with attached contacts.

DESCRIPTION OF THE PREFERRED EMBODIMENT

Figure 5:
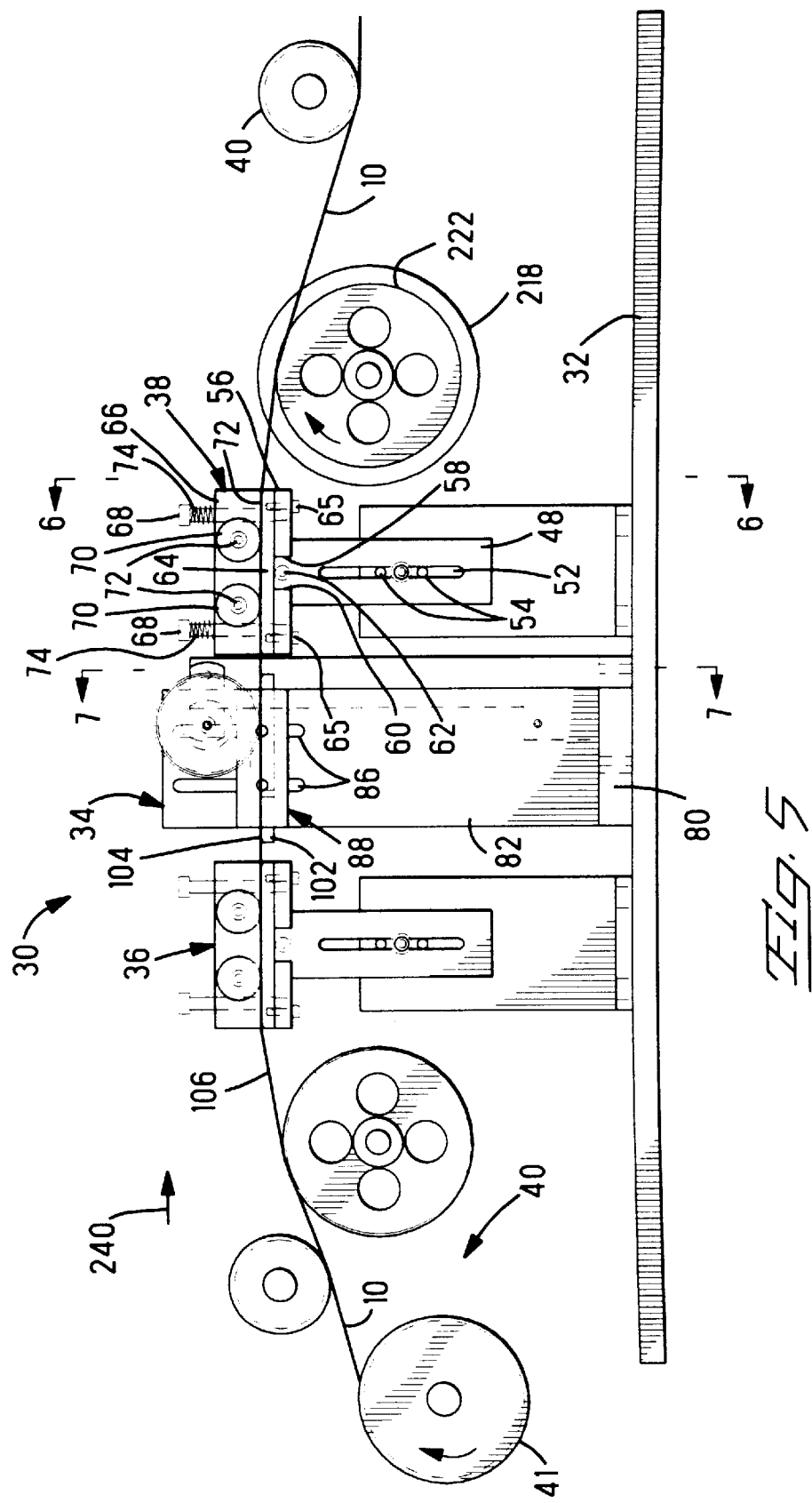
FIG. 5 is a front view of a machine incorporating the teachings of the present invention.

There is shown in FIG. 5 a machine 30 having a frame 32, an anomaly detection unit 34, left and right dampener units 36 and 38, respectively, and a conveyer or transport system 40 which draws the carrier strip 10 from a reel 41, or other source such as the output of a stamping and forming machine, and feeds the carrier strip through the dampener and detection units. As best seen in FIGS. 5 and 6, the right dampener unit 38 includes a base 42 having a pair of flanges 44 extending from opposite sides that are attached to the frame 32 by means of screws 46 extending through holes in the flanges and into threaded holes in the frame. A pair of support plates 48 are attached to opposite sides of the base 42 by means of screws 50 that extend through elongated holes 52 formed in the support plates and into threaded holes in the base as shown. A pair of pins 54 extend outwardly from the base 42 and into the elongated hole 52 of one of the support plates 48 to hold the support plates square with respect to the machine. A dampener plate 56 includes a pair of notches 58 formed in opposite sides thereof for receiving a necked down end 60 of each support plate 48. Each screw 62 extends through a hole in the necked down end and into a threaded hole in the dampener plate 56 to secure the parts tightly together. A feed track member 64 is attached to the upper surface of the dampener plate 56 for supporting and guiding the carrier strip 10. Screws 65 extend through holes in the dampener plate 56 and into threaded holes in the feed track member 64 to secure it in place. A dampener block 66 is arranged to slide vertically on two shoulder screws 68 that are tightly threaded into holes in the dampener plate 56. Two rollers 70 are journaled for rotation on respective shafts 72 that extend outwardly from press fit holes in the dampener block 66. The two rollers 70 are positioned so that they engage an upper guide surface 72 of the feed track member 64. When the carrier strip 10 is fed into the machine 30, it is sandwiched between the rollers 70 and the upper guide surface 72. Each shoulder screw 68 includes a compression spring 74 that urges the dampener block 66 downwardly, while a pair of compression springs 76 are arranged between the dampener plate 56 and the underside of the dampener block 66 to urge the dampener block upwardly somewhat to balance the dampener unit and minimize bounce and other vibration of the rollers 70. The left dampener unit 36 is substantially similar to the right dampener unit 38 and, therefore, will not be described further.

The anomaly detection unit 34, as best seen in FIG. 5 and 7, includes a base 80 having a pair of upright support plates 82 extending from opposite sides of the base and attached thereto by means of screws 78 that are arranged in counterbored holes in the base and threaded into holes in the edges of the two support plates. The base 80 is attached to the frame 32 by means of screws 84 extending through elongated holes in the base and into threaded holes in the frame. A pair of spaced elongated holes 86 are formed in the upper end of each support plate 82, as best seen in FIG. 5. A sensor unit 88 is attached to the upper ends of the support plates by means of four screws 90, shown in FIG. 7, that extend through the elongated holes 86 and into threaded holes in the sensor unit. The elongated holes permit vertical adjustment in the position of the sensor unit. The sensor unit 88, as best seen in FIGS. 8, 9, and 10, is a rectangular shaped plate 92 having an elongated opening 94 formed completely through the plate on a longitudinal axis 96, as best seen in FIG. 9. A slot 98 is formed through an upper portion of the plate 92 so that the slot intersects the elongated opening 94 for a purpose that will be explained. A pair of threaded holes 100 are formed in opposite sides of the plate 92, two of which are for receipt of the screws 90. A guide track member 102 having an upper guide surface 104, similar to the feed track member 64, is positioned within the elongated opening 94 so that the member extends outwardly on both sides of the plate 92, as shown in FIG. 5. The guide track member 102 serves to support and accurately position the carrier strip 10 and contacts 14, 16, 17, and 18 as the carrier strip is fed through the elongated opening 92 along a feed path 106 that coincides with the longitudinal axis 96, during operation of the machine 30. The guide track member 102 is secured in place by means of screws 108 that extend through holes in the bottom side of the plate 92 and into threaded holes in the guide track member. The guide track member 102 has been omitted from FIGS. 8, 9, and 10 for clarity.

Five light source and photodetector pairs, known as through beam sensors, are arranged in pairs of aligned holes formed in the plate 92, all of which intersect the elongated opening 94 as shown in FIGS. 8, 9, and 10. Certain photodetectors that are designed to be taught when a contact is present or absent, are not recommended for this application because they are very difficult to teach when the contacts are very small and close together. In these cases it is likely that the device will be misprogrammed to be too sensitive or not sensitive enough to the presents of contacts. Banner Engineering of 9714 Tenth Avenue North, Minneapolis, Minn. 55441, manufactures a suitable through beam sensor having part number D12SN6FP which is a small DIN-rail mountable light and photodetector pair with an internal amplifier and discrete logic outputs that can be mated with a variety of optical fibers. In the present example, each of the light sources includes a small diameter fiber optic bundle for narrowing the effective diameter of the beam of light. This effective diameter should not be greater than the width of the smaller of the contacts 14 and 16 to ensure that the contact being checked will completely block the light from the corresponding photodetector while reducing the possibility of any adverse affects caused by a misaligned adjacent contact.

A first left light source 116 and corresponding first left photodetector 118 are arranged perpendicular to the axis 96 and are positioned to intersect a left portion 120 of the feed path 106 through which the left electrical contacts 14 and 16 pass, as shown in FIGS. 9 and 10. A first right light source 124 and corresponding first right photodetector 126 are arranged perpendicular to the axis 96 and are positioned to intersect a right portion 128 of the feed path 106 through which the right electrical contacts 17 and 18 pass, as best seen in FIGS. 8 and 9. A center light source 132 and corresponding center photodetector 134 are arranged perpendicular to the axis 96 and are positioned to intersect that axis and a center portion of the feed path 106 through which the pilot holes 26 pass. A second left light source 136 and corresponding second left photodetector 138 are arranged at an angle 140 to the axis 96, shown in FIG. 10, of 63 degrees and 22 minutes and are positioned to intersect the left portion 120 of the feed path 106 through which the left electrical contacts 14 and 16 pass, as shown in FIGS. 9 and 10. The angle 140 of 63 degrees and 22 minutes is important in the measuring of the Z-axis distances for the contacts 14, 16, 17, and 18 of the carrier strip 10 because of the overlap condition provided by these two adjacent contacts 14-1 and 16-2 at that angle, as shown in FIG. 17. One contact may completely overlap the other or it may only partially overlap, but in either case the two contacts will appear as a single contact to the photodetector 138, as will be explained below. It is desirable to have these two overlapping contacts appear as a single wide contact because it reduces by fifty percent the number of apparent contacts that the photodetector 138 will detect thereby reducing processing time needed to calculate the Z-axis distances. If, however, the angle 140 were made too small then contacts that are not immediately adjacent would begin to overlap making the sensor signals difficult to interpret In the case of the contacts 24 of the carrier strip 20 where there is no overlap of the contacts, the angle 140 can be much smaller and, therefore, will provide a more direct Z-axis distance measurement. In any case, the angle 140 should be between about 20 degrees and about 70 degrees, depending upon the application. A second right light source 144 and corresponding second right photodetector 146 are arranged at an angle 140 to the axis 96 of 63 degrees and 22 minutes and are positioned to intersect a right portion 128 of the feed path 106 through which the right electrical contacts 17 and 18 pass, as best seen in FIGS. 8 and 9. Each of the light sources 116, 124, 132, 136, and 142 have electrical leads 146 extending therefrom that are interconnected to a suitable power supply, not shown. Additionally, each of the photodetectors 118, 126, 134, 138, and 144 have electrical leads 148 that are interconnected to appropriate detector circuitry that will be described below.

The detection unit 34 includes a vibration dampener 154, as best seen in FIGS. 7 and 11. It includes a bass 156 having a mounting flange 158 that is attached to the frame 32 by means of screws 160 that extend through elongated holes in the flange and into threaded holes in the frame. A pivot shaft 162 is pivotally supported in the top end of the base 156 and has a swing arm 164 attached to one end thereof and another swing arm 166 attached to the other end, as best seen in FIG. 11. The swing arm 164 includes a shaft 168 journaled for rotation therein that extends outwardly directly over the sensor unit 88. A dampener roller 170 is attached to the end of the shaft 168 and is positioned so that the roller enters the slot 98 and engages the upper guide surface 104. When the carrier strip 10 is fed into the machine it is sandwiched between the roller 170 and the upper guide surface 104. As the carrier strip 10 is moved along the feed path 106 it is urged against the guide surface 104 by the roller 170. The free end of the other swing arm 166 is biased downwardly, as viewed in FIG. 7, by means of an extension spring 172 having one end secured to a pin 174 that extends from the swing arm and the other end secured to a pin 176 extending from the base 156, as shown in FIG. 7. The characteristics of the spring 172 are chosen to effect maximum dampening on the carrier strip 10 as it moves through the sensor unit 88.

Figure 13:
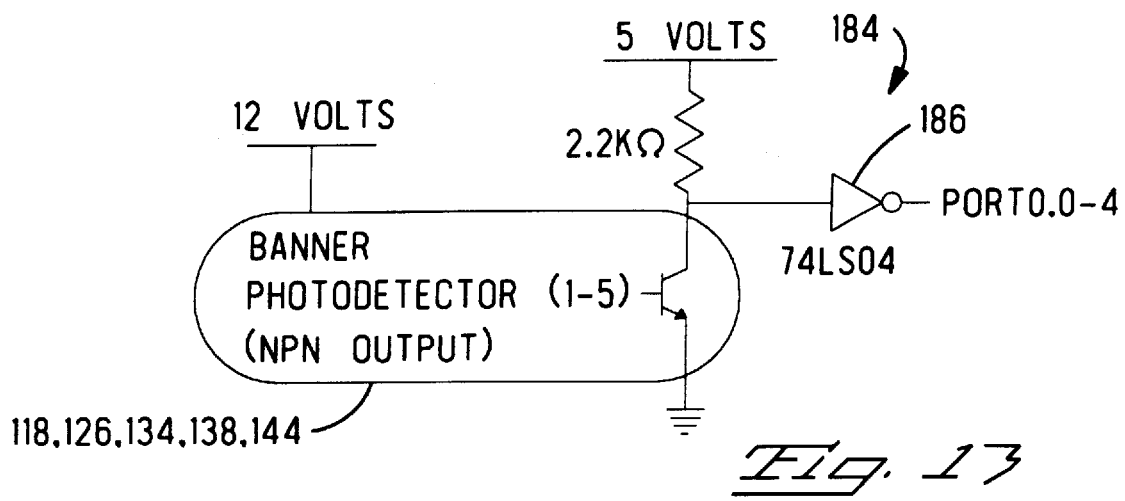
FIGS. 13, 14, and 15 are schematic diagrams showing circuitry for the detector, LED array, and encoder, respectively.
Figure 14:
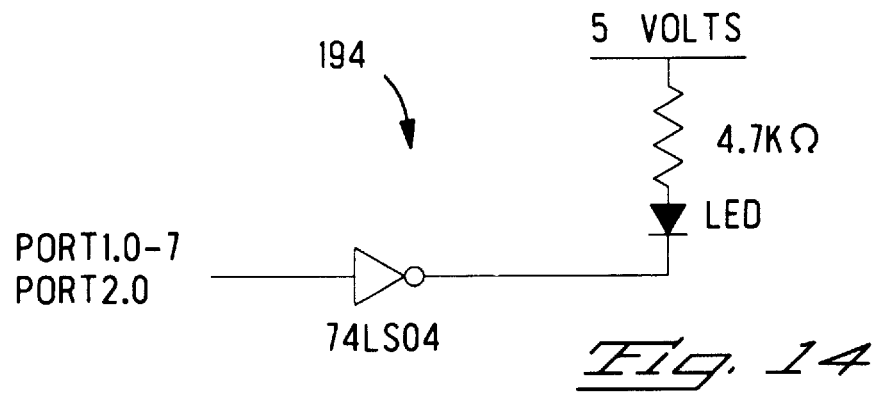
Figure 15:
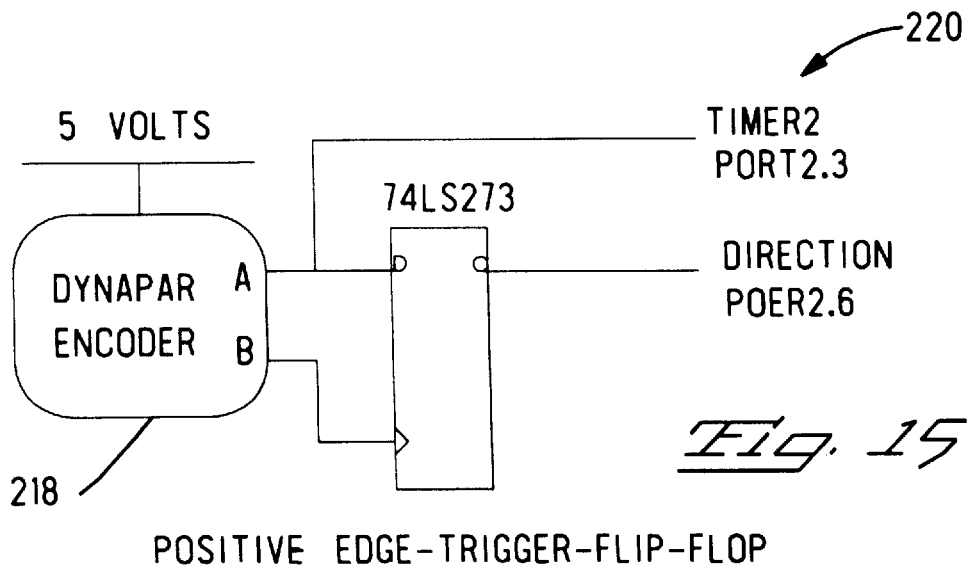

The leads 148 of the photodetectors 118, 126, 134, 138, and 144 are interconnected to a control unit 182 via detector electronics 184, as shown in FIG. 12. The detector electronics 184 is shown in FIG. 13 where it is seen that the output of the photodetector is buffered through an inverter 186 (74LS04). The inverter is necessary because the photodetector has an open collector NPN-type output where an "on" signal from the sensor to the NPN output transistor actually results in the output collector being pulled low so that "on" means zero volts instead of the conventional five volts. The inverter corrects this. The control unit 182 is a 16 bit 80C196 microcontroller that is manufactured by Intel Corporation of 2200 Mission College Boulevard , P.O. Box 58119, Santa Clara, Calif. 95052-8119. The control unit 182 includes a main bus 188 that interconnects three input/output ports 190, 192, and 194, a 16 MHz central processing unit 196, a memory controller 198 that is interconnected to external memory 200, a set of two timers 202, an interrupt controller 204, and a high speed input section 206. A serial interface is provided to interconnect the central processing unit 196 to a host personal computer 208 for use during debugging and making modifications to the system. Additionally, the host PC may be used to enhance error analysis once anomalies are detected and to collect desired statistics. An array of LEDs is interconnected to the second I/O port 192 via suitable LED electronics 212, such as that shown in FIG. 14. The LEDs are used to indicate status of the machine during its operation and, when anomalies are detected, to indicate this fact as well as to display the number of anomalies that have been detected. An encoder 218, as shown in FIG. 12, is interconnected to the third I/O port 194 and includes encoder electronics 220 that is shown in FIG. 15. The encoder 218, a Dynapar model series 523 manufactured by Dynapar Controls of 1675 Delany Road, Gurnee, Ill. 60031-1282, is a high pulse count incremental rotary encoder. It is used to measure the distances between a pilot hole and a contact 14, 16, 17, 18. The encoder produces two square-wave outputs, each with 5000 pulses per revolution of the encoder shaft. These outputs are 90 degrees out of phase and can be used to count at twice the resolution, that is, 10,000 pulses per revolution, by utilizing an up-down edge-triggered counter on board the control unit 182. The encoder 218 is directly coupled to a pin roller 222 having a 2.840 inch diameter, as shown in FIG. 5, which is driven by the moving carrier strip 10. This structure allows the encoder 218 to measure distance to within about 0.00089 inch. In response to every output pulse of the encoder, the encoder electronics 220 will increment an encoder counter when the carrier strip 10 is moved in the forward direction and will decrement the encoder counter when moved in the reverse direction. The value of the encoder counter is used to infer the actual distances between the various edges of the contacts from a respective pilot hole, as will be explained in detail below. It is important that the encoder counter be decremented when the carrier strip 10 is moved in the reverse direction because vibrations or other transient forces present during the operation of the machine 30 may cause such a reversal of direction, only momentarily, that would otherwise increment the encoder counter and result in an erroneous distance reading.

Two interrupts are essential in the implementation of the present invention, a software timer interrupt and a High Speed Input interrupt. The software timer interrupt utilizes one of the timers 202 as a 16 bit free running timer combined with the interrupt hardware to initiate regular sampling of the outputs of the first and second left photodetectors 118 and 138 and the first and second right photodetectors 126 and 144. These are the sensors that detect the electrical contacts 14, 16, and 17, 18, respectively, as they move past the photodetectors When a contact moves to block the beam of light the associated photodetector produces a negative signal and when the contact moves away to allow the beam of light to pass unobstructed the photodetector produces a positive signal. It will be understood that the convention used herein whereby a positive signal is generated when a photodetector receives light from its respective light source and a negative signal is generated when the photodetector does not receive light is arbitrary and is by way of example only. It will be understood that the teachings of the present invention may be practiced with other types of signals that indicate the presence or absence of light emanating from the light source.

The timer is set to cause an interrupt every 56 microseconds so that the first I/O port 190 is sampled and the present position of the encoder 218 for each input is noted. This represents a distance measurement for each edge of a contact that is detected with respect to a previously recorded position of a pilot hole 26. Any differences between these present measurements and the measurements taken during the last sampling are compared with a standard tolerance range and, if outside of the range, are recorded. The sampling rate of 56 microseconds allows the carrier strip 10 to be fed up to a rate of about 89 feet per minute However, any suitable sampling rate may be used. The high speed interrupt is effected by the High Speed Inputs module 206 and is triggered by an "ON" signal, or positive signal, from the center photodetector 134, which indicates that a pilot hole 26 has just been sensed. When this occurs the present position of the encoder 218 is recorded and is used to define the distances to contacts that are subsequently sensed as set forth above. The handler for this interrupt is triggered every time the beginning of a pilot hole is found. It makes a pass/fail decision at this time about the position of the contacts 14, 16, 17, and 18 with respect to the preceding pilot hole 26. It also resets the encoder counter as well as all other variables used to record the present positions of the contacts being examined. Thus, the pilot hole 26 is the starting reference point for the measurement of the positions for the four contacts that follow, two contacts on each side of the carrier strip 10. As the carrier strip is moving, the position of a contact is measured by recording the value of the counter associated with the encoder 218 when the contact triggers one of the photodetectors 118, 126, 138, 144. Note that this is not an absolute measurement of the position of the contact but, rather, is a relative measurement of the position of the contact with respect to the previous pilot hole. The measurement will have some constant offset due to the position of the photodetectors with respect to one another. Further, measurement of the Z-axis by the photodetectors 138 and 144 is not made directly since the effective beam of light is on a 63.4 degree angle. This rather is made by measuring the horizontal translation of a vertical deformation of the contact. For good contacts their relative positions will be within some range, a different range for each different measurement. A deformed contact is one that exceeds any one of these measurements. For every measurement cycle there are eight different measurements made involving four contacts, two contacts on each side of the carrier strip 10. The measurements, taken with respect to the last encountered pilot hole, are used to check for both vertical deformation and lateral deformation of the contacts. The eight measurements are: X-axis, left side first contact; X-axis, right side first contact; X-axis, left side second contact; X-axis, right side second contact; Z-axis, left side front edge of double contact image; Z-axis, right side front edge of double contact image; Z-axis, left side back edge of double contact image; and Z-axis, right side back edge of double contact image. The X-axis measurements are taken by photodetectors 118 and 126 while the Z-axis measurement are taken by the photodetectors 138 and 144. When taking a measurement along the Z-axis, two contacts are normally overlapping and appear as a single contact. The leading or front edge of the image is checked as well as the trailing or back edge of the image in the event that a vertically deformed contact changes the position of only one of the two edges of the image. Each of the eight measurements is compared to a predetermined standard value that represent a nondeformed contact. Each standard value is provided with an acceptable tolerance range. If tile measurement falls within the tolerance range then the contact associated with the measurement is deemed nondeformed. If it falls outside of the range the contact is deemed deformed and an error signal is displayed on the LED array 210.

Figure 16:
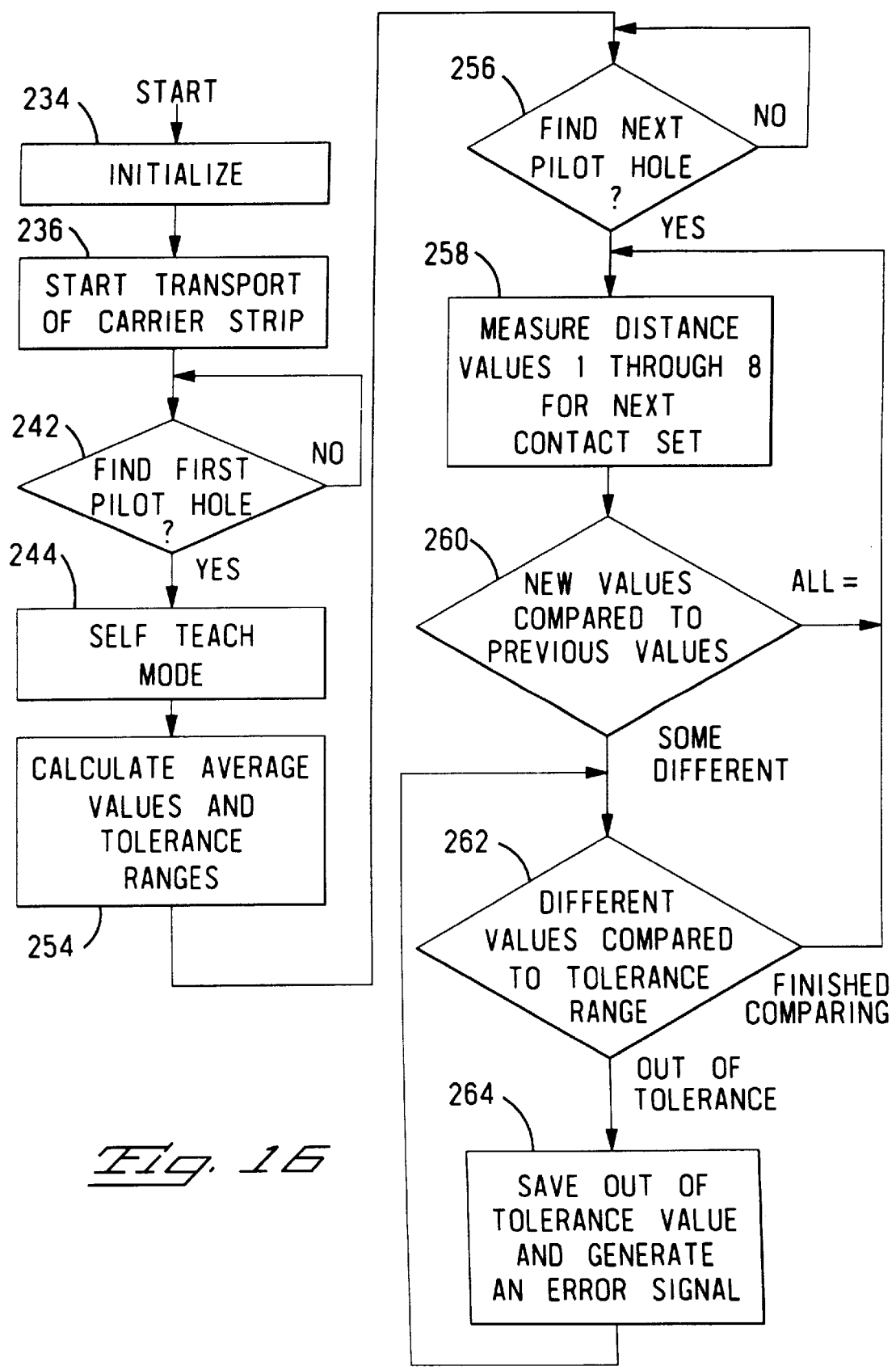
FIG. 16 is a logic flow chart illustrating the operation of the machine.

The operation of the machine 30 will now be describe with reference to FIGS. 5, 16, and 17. When the machine is turned on the control unit is automatically initialized, as indicated at 234 in FIG. 16. A carrier strip 10 is threaded through the left dampener unit 36, the sensor unit 88, and the right dampener unit 38, as shown in FIG. 5. The pin roller 222 is in driven engagement with the pilot holes 26 of the carrier strip 10. The transport system 40 is then started, as indicated at 236 in FIG. 16, to begin moving the carrier strip 10 along the feed path 120 from left to right in the direction of the arrow 240 as shown in FIGS. 5 and 17. At this point the beam of light 238 from the light source 132 is blocked by the carrier strip 10. When the edge of a pilot hole 26 reaches the beam 238, as shown in FIG. 17, the photodetector 134 senses the light indicating that the first pilot hole has been detected, as indicated at 242 in FIG. 16. The control unit 182 then enters into a self teach mode where the four X-axis measurements and the four Z-axis measurements are collected for 32 contacts on each side of the carrier strip 10, as indicated at 244 in FIG. 16. The following discussion will be limited to the contacts on the left side of the carrier strip in the interest of clarity. It will be understood, however, that in actual operation the contacts on the right side will also be examined in a similar manner. Upon sensing the light beam 238 the photodetector 134 produces a positive signal that causes the control unit to reset certain variables and record the present value of the encoder counter. As the carrier strip 10 continues to move toward the right, as viewed in FIG. 17, the light beam 246 from the light source 116 becomes blocked by the contact 16-1 and the photodetector 118, in response to this, produces a negative signal that causes the control unit to record the present value of the encoder counter as representing the Z-axis distance of this contact from the pilot hole 26. Additionally, as the front edge 248 of the lead contact 16-2 and the front edge 249 of the trailing contact 14-1 break the light beam 250 the photodetector 138 produces a negative signal causing the control unit to record the present value of the encoder counter as representing the Z-axis distance of the front edge of the contact 16-2. As movement of the carrier strip continues the contacts 14-1 and 16-2 move from their positions shown in solid lines to positions shown in phantom lines, in FIG. 17. During this movement the two contacts 14-1 and 16-2 overlap so that the light beam 250 remains unbroken until the back edge 252 of the contact 14-1 and the back edge 253 of the contact 16-2 both clear the light beam. At this point the photodetector 138 produces a positive signal causing the control unit 182 to record the present value of the encoder counter as representing the Z-axis distance of the back edges 252 and 253 of these contacts. Note that the angle 140 is chosen so that the two contacts 14-1 and 16-2 completely overlap with respect to the light beam 250, however, it may be advantageous for the two contacts to only partially overlap thereby presenting a wider apparent contact surface to the light beam. It is important that the angle 140 be reasonably shallow to allow for detection of small contact displacements in the Z direction. Similarly, the front edge of the contact 14-2 is detected by the photodetector 118 and its representative X-axis distance is recorded. This process is repeated until the distances have been measured and recorded for all 32 contacts on each side of the carrier strip. The 32 sets of X-axis and Z-axis measurements are then averaged resulting in eight distance values that are now recorded as standard values A plus or minus tolerance range is calculated using a variable, that may be supplied by an operator, for each of the eight distance values and recorded, as indicated at 254 in FIG. 16. As movement of the carrier strip 10 continues the edge of the next pilot hole 26 reaches the beam 238, as shown in FIG. 1. The photodetector 134 senses the light indicating that the next pilot hole has been detected, as indicated at 256 in FIG. 16, and produces a positive signal that causes the control unit to reset certain variables and record the present value of the encoder counter. The control unit 182 then enters into normal run mode where the four X-axis measurements and the four Z-axis measurements are collected for the next two contacts on each side of the carrier strip 10, as indicated at 258 in FIG. 16, and are compared with the previous eight measurements that were taken, as indicated at 260 in FIG. 16. If there are no differences then the control unit 182 loops back and waits for the next set of contacts to be detected by the photodetectors 118 and 126 and then the four X-axis measurements and the four Z-axis measurements are collected for these next two contacts, as indicated at 260, and again compared with the previous eight measurements Whenever another pilot hole 26 is detected by the photodetector 134 a positive signal is produced that causes the control unit to reset certain variables and record the present value of the encoder counter so that subsequent distance measurements will be taken with respect to this pilot hole. This loop continues until one or more of the newly measured distance values are different from their respective previously measured values. When a distance value is different it is compared with the standard distance value for that particular contact position to determine whether or not it falls within the tolerance range established for that standard value, as indicated at 262 in FIG. 16. If it falls outside of the tolerance range the out of tolerance value will be recorded and an error signal will be displayed on the LED array 210 by the control unit 182, as indicated at 264 in FIG. 16. Additionally, the total number of distance measurements that fall outside of their respective tolerance range is indicated on the LED array. At this point the control unit 182 loops back to wait for additional contacts 14, 16, 17, and 18 to be detected by the photodetectors 118 and 126 and for additional pilot holes 26 to be detected by the photodetector 134, as indicated at 258 and 256, respectively, in FIG. 16. This process continues until the end of the carrier strip is encountered or until the machine operator terminates the operation. Any contacts having an X-axis or Z-axis distance measurement that falls outside of the standard range is considered as having an anomaly and may be physically identified by means of a die or other visual mechanism that lends itself to automatic application. Where the distance values fall within the tolerance range the contact is considered to be acceptable.

An important advantage of the present invention is that simple light sources and photodetectors are utilized to effectively detect and identify misaligned contacts without the need for complex vision system components. Further, the present system is relatively inexpensive to make and will function properly with very small closely space contacts.

I claim:
1. In a method of identifying anomalies in a plurality of spaced parts attached to a common carrier strip wherein said carrier strip includes a plurality of spaced pilot holes having a known center to center spacing, said anomalies comprising a deformation of one or more of said parts with respect to others of said parts, comprising the steps:
 (1) transporting said carrier strip and attached parts along a feed path;
 (2) providing a first light source and first photodetector pair arranged on opposite sides of said feed path, and causing light from said first light source to extend along a first line disposed at a first angle to said feed path, in alignment with a portion of said feed path traversed by said plurality of pilot holes so that when a pilot hole is moved into alignment with said first line said first photodetector generates a first positive signal;
 (3) providing a second light source and second photodetector pair arranged on opposite sides of said feed path and causing light from said second light source to extend along a second line disposed at a second angle to said feed path and through a portion of said feed path traversed by said parts so that when a said part interrupts said light said second photodetector generates a second negative signal in response thereto and when said light is not interrupted by a said part said second photodetector generates a second positive signal;
 (4) providing a third light source and third photodetector pair arranged on opposite sides of said feed path and causing light from said third light source to extend along a third line disposed at a third angle to said feed path that is different from said second angle and through a portion of said feed path traversed by said parts so that when a said part interrupts said light said third photodetector generates a third negative signal in response thereto and when said light is not interrupted by a said part said third photodetector generates a third positive signal;
 (5) identifying said anomalies in response to said first and third positive signals and said second and third negative signals; and
 (6) signaling said identifying of said anomalies by generating an error signal.
2. The method according to claim 1 wherein said third angle in step (4) is between about 20 degrees and about 70 degrees.
3. The method according to claim 2 wherein said second angle in step (3) is about 90 degrees and said third angle in step (4) is about 63.4 degrees.
4. The method according to claim 1 wherein said identifying of said anomalies of step (5) includes the steps:
 (5.1) in response to said first positive signal and a subsequent second negative signal, determining the distances between said pilot hole corresponding to said first positive signal and a front edge of said part corresponding to said second negative signal,
 (5.2) in response to said first positive signal and a subsequent third negative signal, determining the distances between said pilot hole corresponding to said first positive signal and a front edge of said part corresponding to said third negative signal, and
 (5.3) in response to said first positive signal and a subsequent third positive signal, determining the distances between said pilot hole corresponding to said first positive signal and a back edge of said part corresponding to said third positive signal,

(5.4) compare each of said determined distances with a corresponding range of standard distance, and if outside said range of standard distance then indicate the presence of an anomaly with respect to said determined distance.

5. The method according to claim 4 wherein said determining the distances is accomplished by:

determining the speed of said transporting of said carrier strip along said feed path;

determining the time interval between the time that said first positive signal is generated and the time that one of the second negative signal, the third negative signal, and the third positive signal, is generated and multiply said time interval by the speed.

6. The method according to claim 4 including the step of providing an encoder having an encoder shaft coupled to and rotationally driven by said carrier strip during said transporting along said feed path, and wherein said determining the distances includes the steps:

recording the instantaneous position of said encoder shaft in response to said first positive signal;

receiving the instantaneous position of said encoder shaft in response to one of said second and third positive signals and said third negative signal, and subtracting said recorded instantaneous position from said received instantaneous position.

7. The method according to claim 1 after step (4) and prior to step (5) including the steps:

(4.1) in response to said first positive signal and a subsequent second negative signal, determining the distances between said pilot hole corresponding to said first positive signal and a front edge of said part corresponding to said second negative signal and store as distance1, (4.2) in response to said first positive signal and a subsequent third negative signal, determining the distances between said pilot hole corresponding to said first positive signal and a front edge of said part corresponding to said third negative signal and store as distance2, and (4.3) in response to said first positive signal and a subsequent third positive signal, determining the distances between said pilot hole corresponding to said first positive signal and a back edge of said part corresponding to said third negative signal and store as distance3, (4.4) performing steps (4.1) through steps (4.3) a plurality of times to produce a plurality of distance1s, a plurality of distance2s, and a plurality of distance3s, then calculating average values for each of said distance1s, distance2s, and distance3s, calculating an upper and lower range for each average value of said distance1s, said distance2s, and said distance3s, storing said calculated average values and said calculated upper and lower values as a range of standard distances, one said range of standard distance for each of said distance1, distance2, and distance3.

8. In a method of identifying anomalies in a plurality of spaced parts attached to a common carrier strip wherein said carrier strip includes a plurality of spaced pilot holes, said anomalies comprising a misalignment or deformation of one or more of said parts, comprising the steps:

(1) transporting said carrier strip and attached parts along a feed path;

(2) providing a first light source and first light detector pair arranged on opposite sides of said feed path for detecting a pilot hole moving along said feed path and causing said first light detector to generate a first positive signal upon said detection of said pilot hole;

(3) providing a second light source and second light detector pair arranged on opposite sides of said feed path so that light from said second light source extends along a line disposed at a first angle to said feed path for detecting a front edge of said part moving along said feed path, and causing said second light detector to generate a second negative signal upon said detection of said front edge;

(4) providing a third light source and third light detector pair arranged on opposite sides of said feed path so that light from said third light source extends along a line disposed at a second angle to said feed path that is different from said first angle, for detecting a front edge of said part moving along said feed path and causing said third light detector to generate a third negative signal upon said detection of said front edge, and for detecting a back edge of said part moving along said feed path and causing said third light detector to generate a third positive signal upon said detection of said back edge;

(5) identifying said anomalies in response to said first and third positive signals and said second and third negative signal; and (6) signaling said detection of said anomalies by generating an error signal.

9. The method according to claim 8 wherein said third angle in step (4) is between about 20 degrees and about 70 degrees.

10. The method according to claim 9 wherein said second angle in step (3) is about 90 degrees and said third angle in step (4) is about 63.4 degrees.

11. The method according to claim 8 wherein said identifying of said anomalies of step (5) includes the steps:

(5.1) in response to said first positive signal and a subsequent second negative signal, determining the distances between said pilot hole corresponding to said first positive signal and a front edge of said part corresponding to said second negative signal, (5.2) in response to said first positive signal and a subsequent third negative signal, determining the distances between said pilot hole corresponding to said first positive signal and a front edge of said part corresponding to said third negative signal, and (5.3) in response to said first positive signal and a subsequent third positive signal, determining the distances between said pilot hole corresponding to said first positive signal and a back edge of said part corresponding to said third positive signal, (5.4) compare each of said determined distances with a corresponding range of standard distance, and if outside said range of standard distance then indicate the presence of an anomaly with respect to said determined distance.

12. The method according to claim 11 wherein said determining the distances is accomplished by:

determining the speed of said transporting of said carrier strip along said feed path;

determining the time interval between the time that said first positive signal is generated and the time that one of the second negative signal, the third negative signal, and the third positive signal, is generated and multiplying said time interval by said speed.

13. The method according to claim 11 including the step of providing an encoder having an encoder shaft coupled to and rotationally driven by said carrier strip during said transporting along said feed path, and wherein said determining the distances includes the steps:

recording the instantaneous position of said encoder shaft in response to said first positive signal;

receiving the instantaneous position of said encoder shaft in response to one of said second and third positive signals and said third negative signal, and subtracting said recorded instantaneous position from said received instantaneous position.

14. The method according to claim 8 after step (4) and prior to step (5) including the steps:

(4.1) in response to said first positive signal and a subsequent second negative signal, determining the distances between said pilot hole corresponding to said first positive signal and a front edge of said part corresponding to said second negative signal and store as distance1, (4.2) in response to said first positive signal and a subsequent third negative signal, determining the distances between said pilot hole corresponding to said first positive signal and a front edge of said part corresponding to said third negative signal and store as distance2, and (4.3) in response to said first positive signal and a subsequent third positive signal, determining the distances between said pilot hole corresponding to said first positive signal and a back edge of said part corresponding to said third negative signal and store as distance3, (4.4) performing steps (4.1) through steps (4.3) a plurality of times to produce a plurality of distance1s, a plurality of distance2s, and a plurality of distance3s, then calculating average values for each of said distance1s, distance2s, and distance3s, calculating an upper and lower range for each average value of said distance1s, said distance2s, and said distance3s, storing said calculated average values and said calculated upper and lower values as a range of standard distances, one said range of standard distance for each of said distance1, distance2, and distance3.

15. In a machine for identifying anomalies in a plurality of spaced parts attached to a common carrier strip wherein said carrier strip includes a plurality of spaced pilot holes, said anomalies comprising a deflection or deformation of one or more of said parts with respect to others of said parts and said pilot holes, said machine including a conveyer for transporting said carrier strip and attached parts along a feed path; a detection unit adjacent said feed path arranged to detect said anomalies in said parts; and signaling means responsive to said detection of said anomalies for signaling said detection, wherein said detection unit comprises:

(a) a first light source and first photodetector pair arranged on opposite sides of said feed path, light from said first light source extending along a first line disposed at a first angle to said feed path and through a portion of said feed path traversed by said plurality of pilot holes so that when a said pilot hole is moved into alignment with said first line said first photodetector generates a first positive signal;

(b) a second light source and second photodetector pair arranged on opposite sides of said feed path, light from said second light source extending along a second line disposed at a second angle to said feed path and through a portion of said feed path traversed by said parts and arranged so that when a said part interrupts said light said second photodetector generates a second negative signal; and (c) a third light source and third photodetector pair arranged on opposite sides of said feed path, light from said third light source extending along a third line disposed at a third angle to said feed path that is different from said second angle and through a portion of said feed path traversed by said parts so that when a said part is moved to interrupt said light said third photodetector generates a third negative signal in response thereto and when said light is not interrupted by a said part said third photodetector generates a third positive signal.

16. The machine according to claim 15 wherein said detection unit includes means for identifying said anomalies in response to said first and third positive signals and said second and third negative signals, and wherein said signaling means generates an error signal in response to said identifying said anomalies.

17. The machine according to claim 16 wherein said means for identifying said anomalies comprises a controller arranged to receive said first and third positive signals and said second and third negative signals and to:

(a) in response to said first positive signal and a subsequent second negative signal, calculate the distances between said pilot hole corresponding to said first positive signal and a front edge of said part corresponding to said second negative signal, (b) in response to said first positive signal and a subsequent third negative signal, calculate the distances between said pilot hole corresponding to said first positive signal and a front edge of said part corresponding to said third negative signal, and (c) in response to said first positive signal and a subsequent third positive signal, calculate the distances between said pilot hole corresponding to said first positive signal and a back edge of said part corresponding to said third positive signal, (d) compare each of said calculated distances with a corresponding range of standard distance, and if outside said range of standard distance then indicate the presence of an anomaly with respect to said calculated distance.

18. The machine according to claim 15 wherein said conveyer includes a dampening surface in engagement with said carrier strip and arranged to limit lateral movement of said carrier strip during movement thereof along said feed path.

19. The machine according to claim 18 wherein said dampening surface includes a surface of a stationary member attached to said machine and a surface of a roller rotationally coupled to said machine wherein said carrier strip is sandwiched between said surfaces of said stationary member and said roller.

20. The machine according to claim 15 wherein said detection unit includes a block attached to said machine, said block having a first opening therethrough within which said first light source and first photodetector pair are disposed, a second opening therethrough within which said second light source and second photodetector pair are disposed, a third opening therethrough within which said third light source and third photodetector pair are disposed, and a fourth opening therethrough disposed laterally with respect to said first opening and intersecting each of said first, second, and third openings so that each of said first, second, and third light sources is on an opposite side of said fourth opening from its respective first, second, and third photodetector.

21. The machine according to claim 20 wherein said first, second, and third light sources are on one side of said fourth opening and said first, second, and third photodetectors are on another side of said fourth opening opposite said one side, and wherein said feed path extend completely through said fourth opening.

22. In a machine for identifying anomalies in a plurality of spaced parts attached to a common carrier strip wherein said carrier strip includes a plurality of spaced pilot holes, said anomalies comprising a deformation of one or more of said parts with respect to others of said parts and said pilot holes, said machine comprising:

(a) a conveyer for transporting said carrier strip and attached parts along a feed path;

(b) a first light source and first photodetector pair arranged on opposite sides of said feed path in optical alignment with a first line disposed at a first angle to said feed path and arranged so that when a said pilot hole is moved into alignment with said first line said first photodetector generates a first positive signal in response thereto;

(b) a second light source and second photodetector pair arranged on opposite sides of said feed path in optical alignment with a second line disposed at a second angle to said feed path and arranged so that when a said part is moved into alignment with said second line said part interrupts said light and said second photodetector generates a second negative signal in response thereto;

(c) a third light source and third photodetector pair arranged on opposite sides of said feed path in optical alignment with a third line disposed at a third angle to said feed path that is different from said second angle and arranged so that when a said part is moved into alignment with said third line to interrupt said light said third photodetector generates a third negative signal in response thereto and when said part is moved out of alignment with said third line said third photodetector generates a third positive signal in response thereto; and (d) means for identifying said anomalies in response to said first and third positive signals and said second and third negative signals.

\* \* \* \* \*